(12) United States Patent
Zscheeg

(10) Patent No.: US 7,730,788 B2
(45) Date of Patent: Jun. 8, 2010

(54) METHOD OF MEASURING THE RETENTION FORCE OF A BIOMEDICAL SPECIMEN IN THE FORM OF AN ELECTRICALLY CONDUCTIVE STRUCTURE LOCATED ON A CARRIER

(75) Inventor: Harry Zscheeg, Rielasingen-Worblingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 195 days.

(21) Appl. No.: 11/856,008

(22) Filed: Sep. 14, 2007

(65) Prior Publication Data

US 2008/0134799 A1 Jun. 12, 2008

(30) Foreign Application Priority Data

Sep. 15, 2006 (EP) .................................. 06019385

(51) Int. Cl.
*G01B 7/16* (2006.01)
(52) U.S. Cl. ........................................... 73/779; 73/760
(58) Field of Classification Search ............ 73/760–860
See application file for complete search history.

(56) References Cited

U.S. PATENT DOCUMENTS

| | | | | | |
|---|---|---|---|---|---|
| 3,927,724 | A | * | 12/1975 | Baker | 177/136 |
| 4,017,192 | A | * | 4/1977 | Rosenthal | 356/432 |
| 4,649,907 | A | * | 3/1987 | Whitehead et al. | 602/40 |
| 5,851,218 | A | | 12/1998 | Lev | |
| 6,460,397 | B1 | | 10/2002 | Biehl | |
| 6,615,640 | B2 | * | 9/2003 | Ahn et al. | 73/9 |
| 6,673,102 | B1 | | 1/2004 | Vonesh | |
| 6,682,553 | B1 | | 1/2004 | Webler | |

FOREIGN PATENT DOCUMENTS

| | | |
|---|---|---|
| DE | 19803219 | 8/1999 |
| JP | 2004-177332 | 6/2004 |

OTHER PUBLICATIONS

Bashar et al., "Mechanical Properties of Various Z-Stent Designs: An Endovascular Stent-Grafting Perspective", Artificial Organs, vol. 27, No. 8, Aug. 2003, pp. 714-721.
Rogers C Ritter et al., "Measurement of Friction on Straight Catheters in In Vitro Brain and Phantom Material", IEEE Transactions on Biomedical Engineering, IEEE Service Center, Piscataway, NJ, US, vol. 45, No. 4, Apr. 1998.
Frank G. Shellock, "Biomedical Implants and Devices: Assessement of Magnetic Field Interactions with a 3.0-Tesla MR System", Journal of Magnetic Resonance Imaging, vol. 16, Dec. 2002, pp. 721-732.

* cited by examiner

*Primary Examiner*—Max Noori
(74) *Attorney, Agent, or Firm*—Workman Nydegger

(57) ABSTRACT

A method of measuring the retention force of a biomedical specimen coupled to a carrier includes the measurement of the force required for magnetically decoupling the specimen from the carrier. In one embodiment, the method includes the steps of providing the specimen with an electrically conductive structure; creating an external alternating magnetic field near the specimen; increasing the amplitude and/or frequency of the magnetic field; detecting the start of the movement of the specimen on the carrier; and calculating the retention force of the specimen by determining the applied magnetic force on the basis of the parameters of the magnetic field. In other embodiments, the magnetic field may remain constant and the biomedical specimen may be moved through the field at varying speeds.

18 Claims, 2 Drawing Sheets

METHOD OF MEASURING THE RETENTION FORCE OF A BIOMEDICAL SPECIMEN IN THE FORM OF AN ELECTRICALLY CONDUCTIVE STRUCTURE LOCATED ON A CARRIER

FIELD OF THE INVENTION

The present invention relates to a method of measuring the retention force of a biomedical specimen disposed on a carrier. In one embodiment, the present invention relates to a method of measuring the retention force of a medical device that is coupled to a delivery system by inducing a magnetic force on the device.

BACKGROUND OF THE INVENTION

Medical procedures often require that a biomedical specimen be coupled to a carrier. For example, medical devices such as stents, markers or sleeves are generally coupled to catheters or balloons that deliver the device to a target area where the device is deployed by uncoupling the device from the carrier.

More particularly, a stent may be coupled to a catheter having a balloon at the distal end by crimping the stent on the balloon in deflated condition. The catheter is then introduced in a vessel of a patient and, when a target location is reached, the balloon is inflated, causing the stent to expand and to support the wall of the vessel as desired. Alternatively, a self-expanding stent may be coupled to the distal end of a catheter and be covered by a sheath. The catheter is then introduced in a patient's vessel and, when the target location is reached, the sheath is retracted, enabling the stent to self-expand and scaffold the vessel wall.

In this respect, it is of great importance that the medical device be properly coupled to the carrier, so to avoid the decoupling of the device from the carrier at an undesired location. In the case of a balloon-expanded stent, the stent must be coupled to the balloon and to the catheter with contact force sufficient to create an interference that will prevent the stent from sliding off the balloon while the balloon travels in the patient's vessels along its path to the target location, especially considering that friction with the vessel walls or bends in the vessel system are prone to induce such a decoupling.

An undesired decoupling of the medical device from the carrier would not only render the procedure difficult or impossible to perform, but also lodge the stent at an improper location and require a surgical procedure for removing the misplaced stent.

Known methods and systems for measuring the retention force of a biomedical specimen on a carrier are based on mechanical principles. Such methods and systems are based on mechanically impacting the structure to be measured, thereby negatively affecting the mechanical integrity of the system and a proper reading of the values to be measured. One such mechanical test is a tensile pull test, which determines the mechanical force required to pull the stent off the delivery balloon. Another such test is compressive in nature. These types of mechanical tests are described, for example, in Example 2 of U.S. Pat. No. 6,682,553 and in Example 1 of U.S. Pat. No. 6,673,102.

SUMMARY OF THE INVENTION

Based on the foregoing, it is an object of the present invention to provide a method of measuring the retention force of a biomedical specimen on a carrier without affecting the integrity of the specimen.

It is also an object of the present invention to provide a method of measuring the retention force of a biomedical specimen on a carrier without compromising the quality of the measurement through contacts with the specimen.

These and other objects of the present invention are achieved through a method of measuring the retention force of biomedical specimen on a carrier performed according to the principles of the present invention. The biomedical specimen is provided as an electrically conductive structure and a magnetic field that varies in time and/or spatially is created near the specimen. The amplitude and/or frequency of the magnetic field may be increased until a movement of the specimen on the carrier is detected. The retention force is calculated by measuring the applied magnetic force on the basis of the parameters of the magnetic field applied to the specimen. Alternatively, the magnetic field may remain constant and the specimen may be moved through the field at varying speeds.

A method according to the present invention avoids the aforementioned disadvantages of the prior art because undesirable axial compressive or tensile forces on the specimen are avoided through the use of external force fields that imparts a force on the specimen. Electric currents are induced in the specimen to cause it to behave like an electromagnet, and an external magnetic field is used to impart a force on the specimen such that the specimen becomes prone to slide off the carrier structure, for example, in an axial direction. The force applied to the specimen can be computed from the test parameters (such as current, voltage etc.), and, from the applied force, the retention force of the specimen on the carrier is computed accordingly.

One embodiment of the invention relates to the measurement of the retention force of a stent on a balloon, or, in other words, to the measurement of the threshold force required to activate the decoupling of the stent from the balloon. By detecting the onset of a movement of the stent off the balloon, an indication is provided that the applied force exceeds the retention force.

Another embodiment of the invention relates to the measurement of parameters that cause specimen movement. Such parameters may be manipulated to measure the rate of decoupling of the specimen from the carrier structure. For example, one of the parameters, current, may be varied to control the magnetic field applied to the specimen movement.

Still another embodiment of the invention relates to implementing the method of the present invention by utilizing the following equipment:

a device for generating a magnetic field that varies in time, space or both, for example, an electromagnet;

optionally, a system for detecting specimen movement; and optionally, an electronic feed-back loop that causes the specimen to acquire a constant velocity of displacement by controlling the operating parameters of the magnetic field through measurement of dynamic friction force.

The feed-back loop may be based on an optical movement detection or on another system. Because the current induced in the specimen is dependent on the specimen's impedance, an impedance measurement may also be performed on the specimen so that, when comparing specimens of different impedances, differences in impedance may assist in interpreting the test results.

Electrically conductive structures to which the method of the present invention may be applied include stents, markers, sleeves with or without braiding as used, for example, in delivery systems for self-expandable stents and for biomedical components of the same kind.

BRIEF DESCRIPTION OF THE SEVERAL VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
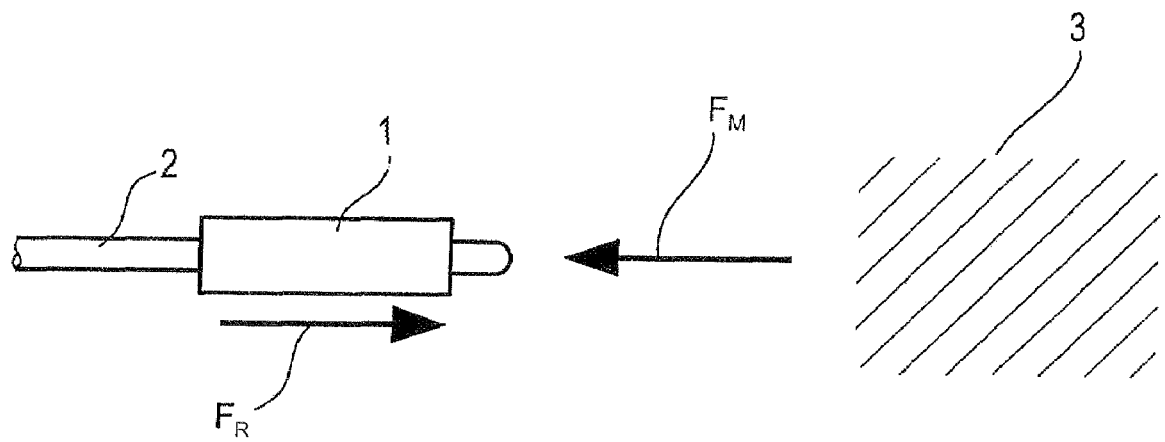
FIG. 1 is a schematic side view of a first embodiment of the invention.

FIG. 1 depicts a schematic side view of a biomedical specimen 1 that has an electrically conductive structure and that is disposed on a carrier 2. In one embodiment, specimen 1 is a stent having a metallic structure, for example, a structure manufactured of stainless steel or Nitinol (a nickel-titanium alloy), and carrier 2 is a balloon catheter, to which the stent is coupled at the distal end. An external alternating magnetic field 3 is created near or around specimen 1, to induce a magnetic force $F_M$ on specimen 1, which is opposed by a retention force $F_R$ coupling specimen 1 with carrier 2. Retention force $F_R$ may be a force of different kinds, but is typically a frictional force that maintains specimen 1 disposed on carrier 2.

In the embodiment depicted in FIG. 1, magnetic force $F_M$ attempts to decouple specimen 1 from carrier 2 by means of the pull exercised by magnetic force 8 on specimen 1. Force $F_R$ instead opposes such decoupling until a threshold level $F_M'$ of force $F_M$ is reached, which exceeds $F_R$ and begins to move specimen 1 relative to carrier 2 in the direction of alternating magnetic field 3. Consequently, retention force $F_R$ is equal to $F_M'$, and can be measured accurately by measuring the time varying magnetic gradient dB/dt, as well as the constituent parameters of $F_M'$, for example, the applied current. Example 1 hereinafter describes this embodiment in greater detail.

Figure 2:
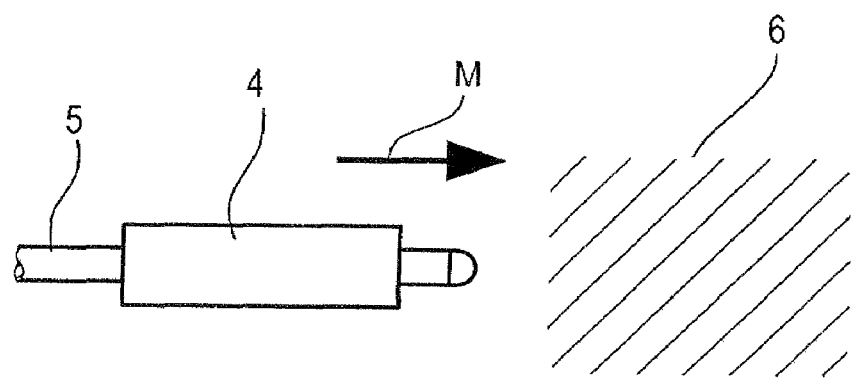
FIG. 2 is a schematic side view of a second embodiment of the invention.

FIG. 2 depicts a schematic side view of a second embodiment of the invention. In this embodiment, a specimen 4 is coupled to a carrier 5, which is moved in the direction of arrow M towards a magnetic field 6 having a constant direction but exhibiting a spatial gradient.

Therefore, the retention force of specimen 4 on carrier 5 is measured not by altering magnetic field 6 over time, but by translating specimen 4 and carrier 5 relative to magnetic field 6, so to expose specimen 5 to a space varying gradient dB/dx. When the point is reached where magnetic force $F_M''$ equals and exceeds the retention force $F_R''$ of specimen 4 on carrier 5, the uncoupling of specimen 4 from carrier 5 begins, thereby providing a measurement of retention force $F_R''$. Example 3 hereinafter describes this embodiment in greater detail.

Figure 3:
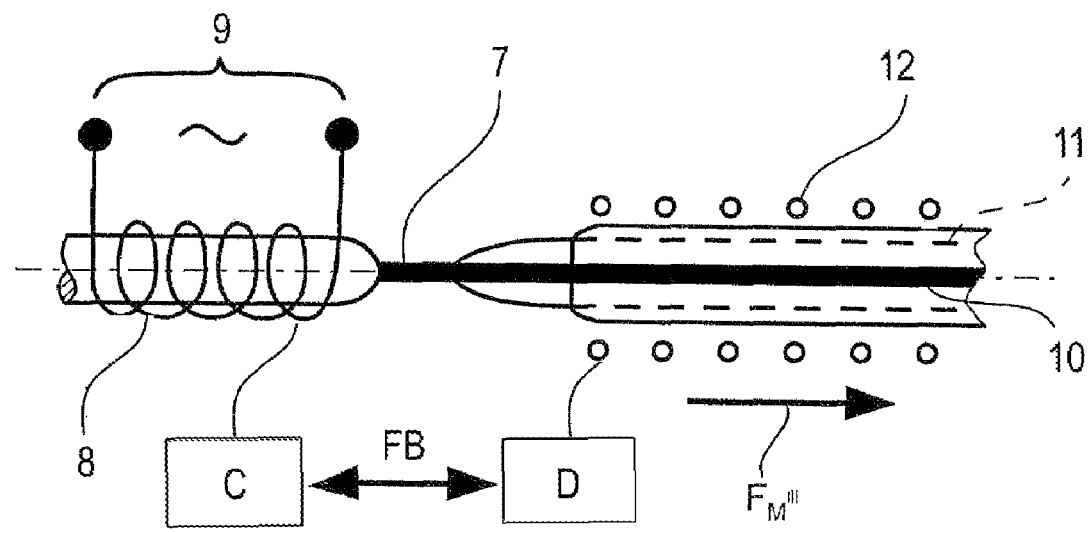
FIG. 3 is a schematic side view of a third embodiment of the invention.

FIG. 3 is a schematic side view of a third embodiment of the invention. In this embodiment, a carrier 7 (for example, a core) is surrounded by a primary coil 8, which is connected to a voltage supply 9. A shaft 10, a catheter 11 and a stent 12 are disposed on carrier 7 at a distance from primary coil 8, making this arrangement comparable to a transformer having a primary coil 8 and a secondary coil that corresponds to stent 12.

Therefore, by supplying alternating current to coil 8, a current is induced in stent 12 having a direction opposite to that of coil 8. This creates a magnetic field opposite to that of primary coil 8. The opposing fields in primary coil 8 and in stent 12 eventually generate a magnetic force $F_M'''$ on stent 12 of sufficient magnitude to initiate the decoupling of stent 12 from catheter 11. Example 2 hereinafter describes this embodiment in greater detail.

FIG. 3 further illustrates that ancillary equipment may be utilized in variants of the present embodiment. Such ancillary equipment may equally be included in variants of any of the embodiments described herein, therefore, the following description may be applicable to all embodiments of the invention.

More specifically, a controller C may be connected to primary coil 8 or to other parts of the system to control magnitude and variations of the magnetic field. For example, controller C may control the amount and characteristics of the electrical current running through coil 8, and changes in time, or space, or time and space of the magnetic field.

A detector D may be connected to stent 12 or other parts of the system to detect and monitor the movements of specimen 12. Detector D may be an optical detector, but other types of detectors that are known in the art may be included.

Further, a feed-back loop FB such as an electronic feedback loop may be included, to cause specimen 12 to acquire a certain amount of current or, in other embodiments of the invention, to have the specimen acquire a predetermined velocity of displacement in relation to the magnetic field.

Figure 4:
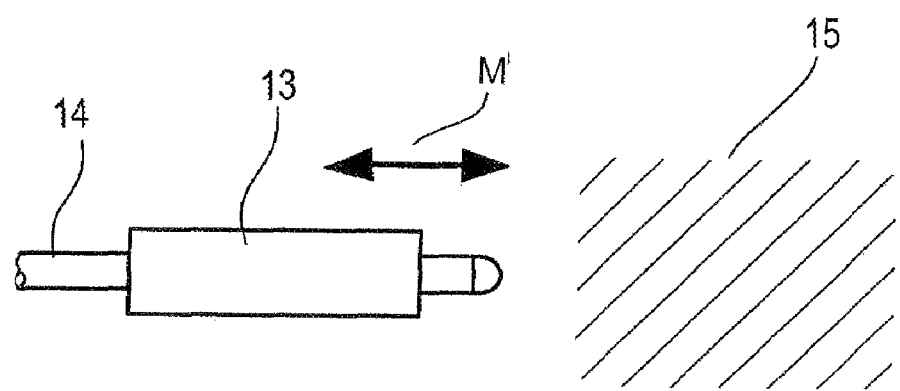
FIG. 4 is a schematic side view of a fourth embodiment of the invention.

FIG. 4 depicts a schematic side view of a fourth embodiment of the invention. A specimen 13 is coupled to a carrier 14 and is also exposed to a magnetic field 15 of constant direction. For example, specimen 13 may be a metallic stent that is coupled to a carrier 14 that may be a balloon catheter. Specimen 13 is exposed to a magnetic field of constant direction and may be brought closer to magnetic field 15 by accelerating the speed of specimen 13, until a speed is reached where a threshold magnetic force $F_M''''$ will start the decoupling of specimen 13 from carrier 14. If such decoupling is not attained, the magnetic field may be increased and the experiment repeated until the decoupling actually initiates. Example 4 hereinafter describes an application of this embodiment in greater detail.

The following examples describe the above embodiments with greater specificity. These examples, however, should not be construed as limiting, but merely as representative of the invention, which may be embodied in a plurality of other systems, structures, and manners.

Example 1

An electromagnet is provided to generate an alternating magnetic field that changes in time. The specimen is disposed near or inside the electromagnet and the amplitude of the magnetic field, or the frequency, or both are increased until the specimen begins to decouple. The magnetic force and thus the operational parameters of the electromagnet needed to start the movement of the specimen relative to the carrier are correlated to the amount of frictional force that holds the specimen in place, thereby providing a measurement of the retention force of the specimen on the carrier.

Example 2

The specimen is disposed on a core and operates as the secondary coil of a transformer, with the primary coil disposed on a straight core or on a different type of core configuration. The core supporting the specimen may be shaped so that an instrument carrying the specimen could be used to dispose the specimen over the core during assembly of the specimen with the carrier. Changing the magnetic field in the primary coil, for example by manipulating the supply voltage, induces a voltage in the specimen and thus a force.

The supply voltage can be switched on and off with stepwise increased amplitude until the specimen begins to decouple from the carrier. The applied voltage amplitude operates as a measure of the retention force of the specimen on the carrier structure.

Example 3

A specimen is disposed on a carrier structure and is moved into a magnetic field having a spatial gradient. The specimen may be moved with a linear drive or with another kind of drive. Instead of moving the specimen, the equipment generating the magnetic field may be moved instead.

The force exerted on the specimen can be increased by increasing the relative velocity until the retention force is reached and the specimen begins to be displaced relative to the carrier structure.

Because the magnetic field need not vary in time but may vary spatially only, permanent magnets may be utilized instead of electromagnets. The permanent magnets provide a spatially varying field due to a varying magnetic strength and/or orientation of their respective north and south poles.

Example 4

The set-up of this example is equivalent to that of Example 3, except that the magnetic field does not have a gradient, but instead the movement of the specimen into the field is accelerated. Thus, an increasing force is generated on the specimen. Moreover, several external magnets may be utilized, providing a better control of the applied forces.

The method of the present invention may be employed with any specimen that is manufactured from or that otherwise includes a material conducting an electric current. Exemplary conductive materials are metals and metal alloys like stainless steel, CoCr alloys, NiTi alloys, NbTa alloys, NbWn alloys, TaWn alloys, Pt, Ir, Au and alloys thereof, as well as dual-layers, tri-layers or multi-layers or blends of any of these materials. Non-metallic materials may also be employed, for example, materials that include carbon fibers.

Only part of the specimen may be electrically conductive, for example, the specimen may include a layer, a core or a braiding made of an electrically conductive material, or the specimen may be manufactured from a composite material.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

The invention claimed is:

1. A method of measuring a retention force of a biomedical specimen in the form of an electrically conductive structure located on a carrier, comprising:
    providing an alternating magnetic field in the proximity of the specimen, thereby inducing a magnetic force on the specimen;
    varying the magnetic field;
    detecting the start of decoupling of the specimen from the carrier; and
    determining the retention force by correlating the magnetic force at the start of the decoupling with the magnetic field at the start of the decoupling.

2. The method of claim 1, wherein varying the alternating magnetic field comprises varying the amplitude of the alternating magnetic field.

3. The method of claim 1, wherein varying the alternating magnetic field comprises varying the frequency of the alternating magnetic field.

4. The method of claim 1, wherein providing the alternating magnetic field comprises providing the alternating magnetic field with one or more electromagnets.

5. The method of claim 1, wherein the biomedical specimen is a stent having a metallic structure.

6. The method of claim 1, wherein providing the alternating magnetic field comprises causing a primary coil to provide the alternating magnetic field, wherein the biomedical specimen has an at least partially conductive tubular shape operating as a secondary coil, and wherein the primary coil and the biomedical specimen are retained at a predetermined distance one from the other.

7. The method of claim 6, wherein the primary coil is disposed on a core.

8. The method of claim 6, wherein varying the magnetic field comprises manipulating a supply voltage to the primary coil.

9. The method of claim 6, further comprising the step of connecting a controller to the primary coil for controlling magnitudes and variations of the magnetic field.

10. The method of claim 6, further comprising the step of providing a detector for detecting the decoupling.

11. A method of measuring a retention force of a biomedical specimen in the form of an electrically conductive structure located on a carrier, comprising:
    providing a magnetic field having a spatial gradient in the proximity of the specimen, thereby inducing a magnetic force on the specimen;
    translating the specimen and the carrier relative to the magnetic field;
    determining a location wherein the specimen starts decoupling from the carrier; and
    determining the retention force by correlating the magnetic force at the start of the decoupling with the magnetic field at the location.

12. The method of claim 11, wherein translating the specimen and the carrier relative to the magnetic field comprises translating with a linear drive.

13. The method of claim 11, wherein translating the specimen and the carrier relative to the magnetic field comprises maintaining the magnetic field in a still position while moving the specimen and the carrier.

14. The method of claim 11, wherein translating the specimen and the carrier relative to the magnetic field comprises maintaining the specimen and the carrier in a still position while moving the magnetic field.

15. The method of claim 11, further comprising the step of increasing the relative velocity of the specimen and the carrier relative to the magnetic field.

16. The method of claim 11, wherein providing the magnetic field comprises providing the magnetic field with one or more electromagnets or one or more permanent magnets.

17. The method of claim 16, wherein the one or more permanent magnets provide the spatial gradient by varying magnetic strength or orientation of the north and south poles.

18. The method of claim 11, wherein the biomedical specimen is a stent having a metallic structure.

* * * * *